United States Patent
Kidwell

(10) Patent No.: US 9,182,365 B2
(45) Date of Patent: Nov. 10, 2015

(54) EXCESS ENTHALPY UPON PRESSURIZATION OF NANOSIZED METALS WITH DEUTERIUM

(71) Applicant: David A. Kidwell, Alexandria, VA (US)

(72) Inventor: David A. Kidwell, Alexandria, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 90 days.

(21) Appl. No.: 13/921,195

(22) Filed: Jun. 18, 2013

(65) Prior Publication Data

US 2013/0280128 A1    Oct. 24, 2013

Related U.S. Application Data

(62) Division of application No. 12/893,325, filed on Sep. 29, 2010, now abandoned.

(60) Provisional application No. 61/246,619, filed on Sep. 29, 2009.

(51) Int. Cl.
| | |
|---|---|
| *B01F 3/06* | (2006.01) |
| *G01N 25/48* | (2006.01) |
| *B01J 21/04* | (2006.01) |
| *B01J 23/42* | (2006.01) |
| *B01J 23/44* | (2006.01) |
| *B01J 23/63* | (2006.01) |
| *B01J 29/04* | (2006.01) |

(52) U.S. Cl.
CPC ............... *G01N 25/48* (2013.01); *B01J 21/04* (2013.01); *B01J 23/42* (2013.01); *B01J 23/44* (2013.01); *B01J 23/63* (2013.01); *B01J 29/04* (2013.01)

(58) Field of Classification Search
None
See application file for complete search history.

(56) References Cited

U.S. PATENT DOCUMENTS

| | | | |
|---|---|---|---|
| 6,746,597 B2 | 6/2004 | Zhou et al. | |
| 7,396,795 B2 | 7/2008 | Reyes et al. | |
| 7,429,358 B1 | 9/2008 | Gross | |
| 2009/0086877 A1* | 4/2009 | Hagelstein et al. | ........... 376/100 |

(Continued)

OTHER PUBLICATIONS

Origin of excess heat generated during loading Pd-impregnated alumina powder with deuterium and hydrogen. By O. Dmitriyeva et al. Thermochimica Acta 543 (2012) 260-266.*

(Continued)

*Primary Examiner* — Melvin C Mayes
*Assistant Examiner* — Colette Nguyen
(74) *Attorney, Agent, or Firm* — US Naval Research Laboratory; Rebecca L. Forman

(57) ABSTRACT

A method for producing excess enthalpy by impregnating metallic precursors on an oxide support that reduces sintering and particle growth; drying the impregnated support at a temperature where the particle growth is minimal; reducing the metallic precursors at a second temperature where the particle growth results in supported metallic particles 2 nm or less in size; and pressurizing the supported metallic particles in the presence of deuterium. The metal particles may comprise palladium, platinum, mixtures thereof, or mixtures of palladium and/or platinum with other elements. Also disclosed is a method for measuring excess enthalpy by placing a test material in a pressure vessel; heating the pressure vessel; evacuating the pressure vessel; introducing deuterium, hydrogen, or both into the pressure vessel; measuring the enthalpy generated during pressurization; again evacuating the pressure vessel; and measuring the enthalpy used during depressurization.

9 Claims, 7 Drawing Sheets

(56) References Cited

U.S. PATENT DOCUMENTS

2009/0129992 A1* 5/2009 Mills .............................. 422/112
2009/0142257 A1* 6/2009 Mills .............................. 423/645
2011/0077145 A1* 3/2011 Kidwell .......................... 502/60

OTHER PUBLICATIONS

Aben, "Palladium Areas in Supported Catalysts Determination of Palladium Surface Areas in Supported Catalysts by Means of Hydrogen Chemisorption," Journal of Catalysis, 10, 224-229 (1968).

Arachi et al, "Alternation of the Pd Lattice in Nano-Sized-Pd/ZrO2 Composite during Hydrogen Absorption," X-ray Absorption Fine Structure (2007) 740-42, American Institute of Physics.

Arachi et al., "Structural analysis of nano-sized-Pd/ZrO2 composite after H(D) absorption," Solid State Ionics, 177, (2006), 1861-64.

Arata et al., "Formation of condensed metallic deuterium lattice and nuclear fusion," Proc. Jpn. Acad., Ser. B (2002) 78 (Ser. B), p. 57.

Chou et al., "Calorimetric Heat of Adsorption Measurements on Palladium," Journal of Catalysis, 104, 1-16 (1987).

Gallezot et al., "X-Ray Diffraction Study of Palladium Y Zeolite Location of Palladium Atoms before and after Hydrogen Reduction," Molecular Sieves, 66-73.

Heung et al, "Hydrogen Isotope Exchange Properties of Porous Solids Containing Hydrogen," WSRC-MS-2004-00089, Aug. 18, 2004.

Huang et al., "Chemical Activity of Palladium Clusters: Sorption of Hydrogen," J. Phys. Chem. B (2006) 110, 21783-87.

Narehood et al., "X-ray diffraction and H-storage in ultra-small palladium particles," International Journal of Hydrogen Energy, 34 (2009) 952-60.

Parchamazad et al., "A Novel Approach to Study Deuterium Desktop Fusion," The 14th International Conference on Condensed Matter Nuclear Science, Aug. 10, 2008.

Sermon, "Characterization of Palladium Blacks I. A Novel Hydrogen Pretreatment and Surface Area Determination of Palladium," Journal of Catalysis 24, 460-66 (1972).

Yamaura et al., "Hydrogen absorption of nanoscale Pd particles embedded in ZrO2 matrix prepared from Zr—Pd amorphous alloys," J. Mater. Res., vol. 17, No. 6, Jun. 2002, 1329-34.

Parchamazad, "LENR with Zeolites," www.youtube.com/watch?v=2L-IKozWjSA, Sep. 30, 2012 (visited Jun. 23, 2015).

* cited by examiner

EXCESS ENTHALPY UPON PRESSURIZATION OF NANOSIZED METALS WITH DEUTERIUM

The present application is a divisional application of U.S. application Ser. No. 12/893,325 filed by David A. Kidwell on Sep. 29, 2010 entitled "EXCESS ENTHALPY UPON PRESSURIZATION OF NANOSIZED METALS WITH DEUTERIUM," now abandoned, which was a non-provisional application that claimed the benefit of provisional application Ser. No. 61/246,619 by David A. Kidwell, filed Sep. 29, 2009 entitled "ANOMALOUS HEAT GENERATION FROM DEUTERIUM (OR PLATINUM) LOADED NANOPARTICLES," the entire contents of each are incorporated herein by reference.

FIELD OF THE INVENTION

The present invention relates generally to gas pressurization of metal particles and more specifically to the pressurization in the presence of deuterium of metal nanoparticles 2 nm or less in size in an oxide matrix.

BACKGROUND OF THE INVENTION

The study of dispersed metals has a long history because of their use as catalysts. It is well-known in the art that as the size of the metal particles decrease, the activity increases. Mainly papers concerning the ratio of hydrogen to palladium atoms and the heats of adsorption of hydrogen into palladium are referenced herein. The rate of organic chemical bond-forming and cracking reactions also vary with particle size, as is well-known in the art. However, that art does not concern the present application. Much of the art references hydrogen reactions, but for the purpose of the present application, hydrogen and deuterium are considered identical in chemical nature for the ratios of uptake with a metal catalyst. For example, others have shown that the uptake of hydrogen increases rapidly when the particle size of the dispersed palladium in an oxide matrix decreases to 1 nm or less. See, e.g., Shu-Chin Chou et al., "Isosteric Heat of Sorption of Dihydrogen on Alumina-supported Palladium," *J. Chem. Soc. Faraday Trans.*, 91, 949-951 (1995); Sheng-Yang Huang et al., "Chemical Activity of Palladium Clusters: Sorption of Hydrogen," *J. Phys. Chem. B*, 110, 21783-21787 (2006), the entire contents of each are incorporated herein by reference. Although, they did not state the particle size specifically, data from Huang, et al., can be used to estimate the particle size and the approximate ratio of H:Pd as shown in Table 1. The heat of adsorption also increased with decreasing particle size. Others have studied a number of supports and preparation conditions and have also showed that the heat of adsorption and loading ratio increased with decreasing particle size. Pen Chou et al., "Calorimetric Heat of Adsorption Measurements on Palladium I. Influence of Crystallite Size and Support on Hydrogen Adsorption," J. of Catalysis, 104, 1-16 (1987), the entire contents of which is incorporated herein by reference. The estimated particle size in Chou's work was greater than 1.6 nm. Aben showed that hydrogen absorption could be used to estimate particle size and that the H:Pd ratio also increased with decreasing particle size, reaching a maximum H:Pd ratio of 0.83 in his study using ion exchanged silica. P. C. Aben, "Palladium areas in supported catalysts: Determination of palladium surface areas in supported catalysts by means of hydrogen chemisorption," Journal of Catalysis, 10 224-229 (1968), the entire contents of which are incorporated herein by reference. The smallest size that Aben measured was 2.5 nm. He also showed that high pretreatment temperatures increased particle growth, which would be detrimental to the present invention.

TABLE 1

Estimated particle sizes and H/Pd ratios as calculated from Huang, et al. Note the sensitive dependence on the loading ratio with particle size. The more chemically accessible particles (>5 nm) show a loading similar to bulk palladium of 0.6.

| Preparation | Estimated Particle Size (nm) | Heat of Hydrogen Adsorption (kJ/mole) | Ratio H:Pd @ 0.2 bar |
|---|---|---|---|
| Pd Powder | 9 | 94 | 0.55 |
| 1.86% Pd/SiO2 (IW) | ~4 | 92 | 0.68 |
| 10% Pd/SiO2 (SG) | 1.1 | 131 | 0.9 |
| 5% Pd/SiO2 (SG) | 1 | 183 | 1.05 |

As the particle size must be small for high H:Pd ratios, one must disperse the particles on a support to keep them from sintering and growing too large. As noted by P. A. Sermon, even heating palladium black (a non-supported form of nanosized palladium) to 98° C. would cause sintering of the particles. P. A. Sermon, "Characterization of palladium blacks: I. A novel hydrogen pretreatment and surface area determination of palladium," J. of Catalysis, 24, 460-466 (1972), the entire contents of which are incorporated herein by reference. Arata (Arata et al., *Formation of Condensed Metallic Deuterium Lattice and Nuclear Fusion*. Proc. Jpn. Acad., Ser. B, 78 (Ser. B): p. 57 (2002), the entire contents of which is incorporated herein by reference) has claimed excess heat when pressurizing a specially-prepared Pd—$ZrO_2$ or Pd—Ni—$ZrO_2$ matrix (Shin-ichi Yamaura et al., "Hydrogen absorption of nanoscale Pd particles embedded in $ZrO_2$ matrix prepared from Zr—Pd amorphous alloys," *J. Mater. Res.*, 17, 1329-1334 (2002), the entire contents of which are incorporated herein by reference). His particles (ca. 5 nm) are on the size level of commercial catalysts. See Yoshinori Arachi et al., "Alternation of the Pd Lattice in Nano-Sized-Pd/$ZrO_2$ Composite during Hydrogen Absorption," *X-ray Absorption Fine Structure—XAFS*13, edited by B. Hedman and P. Pianetta, 2007 American Institute of Physics, pp. 740-742 (2007); Yoshinori et al., "Structural analysis of nano-sized-Pd/ZrO2 composite after H(D) absorption," *Solid State Ionics* 177, 1861-1864 (2006), the entire contents of each are incorporated herein by reference. Furthermore, they sinter during use. Others have attempted to put palladium in zeolites and expose it to deuterium to generate excess enthalpy. See I. Parchamazad et al., "Investigations of Nanoparticle Palladium/Deuterium Systems in Zeolites," Abstract for 14th International Conference on Condensed Matter Nuclear Science", Hyatt Regency, Washington, D.C. Aug. 10-15, 2008, the entire contents of which are incorporated herein by reference. The incorporation of the palladium was through an organic palladium precursor and the support was calcined before use—removing the organics and likely growing the particles. Parchamazad et al. made no mention of the particle size, cycling, nor amount of excess enthalpy was made.

BRIEF SUMMARY OF THE INVENTION

The aforementioned problems are overcome in the present invention which provides a method for producing excess enthalpy by impregnating metallic precursors on an oxide support that reduces sintering and particle growth; drying the impregnated support at a temperature where the particle growth is minimal; reducing the metallic precursors at a second temperature where the particle growth results in supported metallic particles 2 nm or less in size; and pressurizing the supported metallic particles in the presence of deuterium. The metal particles may comprise palladium, platinum, mixtures thereof, or mixtures of palladium and/or platinum with other elements. Also disclosed is a method for measuring excess enthalpy by placing a test material in a pressure vessel; heating the pressure vessel; evacuating the pressure vessel; introducing deuterium, hydrogen, or both into the pressure vessel; measuring the enthalpy generated during pressurization; again evacuating the pressure vessel; and measuring the enthalpy used during depressurization.

Gas pressurization of metal particles (palladium, platinum, etc.) 2 nm or less in size produces anomalous amounts of enthalpy in a reproducible manner. This enthalpy is produced in the presence of deuterium but not in the presence of hydrogen. Part of the observed, excess enthalpy can be calculated to be from D-H exchange—i.e. replacement of hydrogen atoms on the surface of the support with deuterium atoms, which is an exothermic reaction. Many control experiments have ruled out the excess enthalpy as being due to impurities in the deuterium that may be absent in the hydrogen. The source of the remaining excess enthalpy is unknown.

These and other features and advantages of the invention, as well as the invention itself, will become better understood by reference to the following detailed description, appended claims, and accompanying drawings.

DETAILED DESCRIPTION OF THE INVENTION

Figure 1:
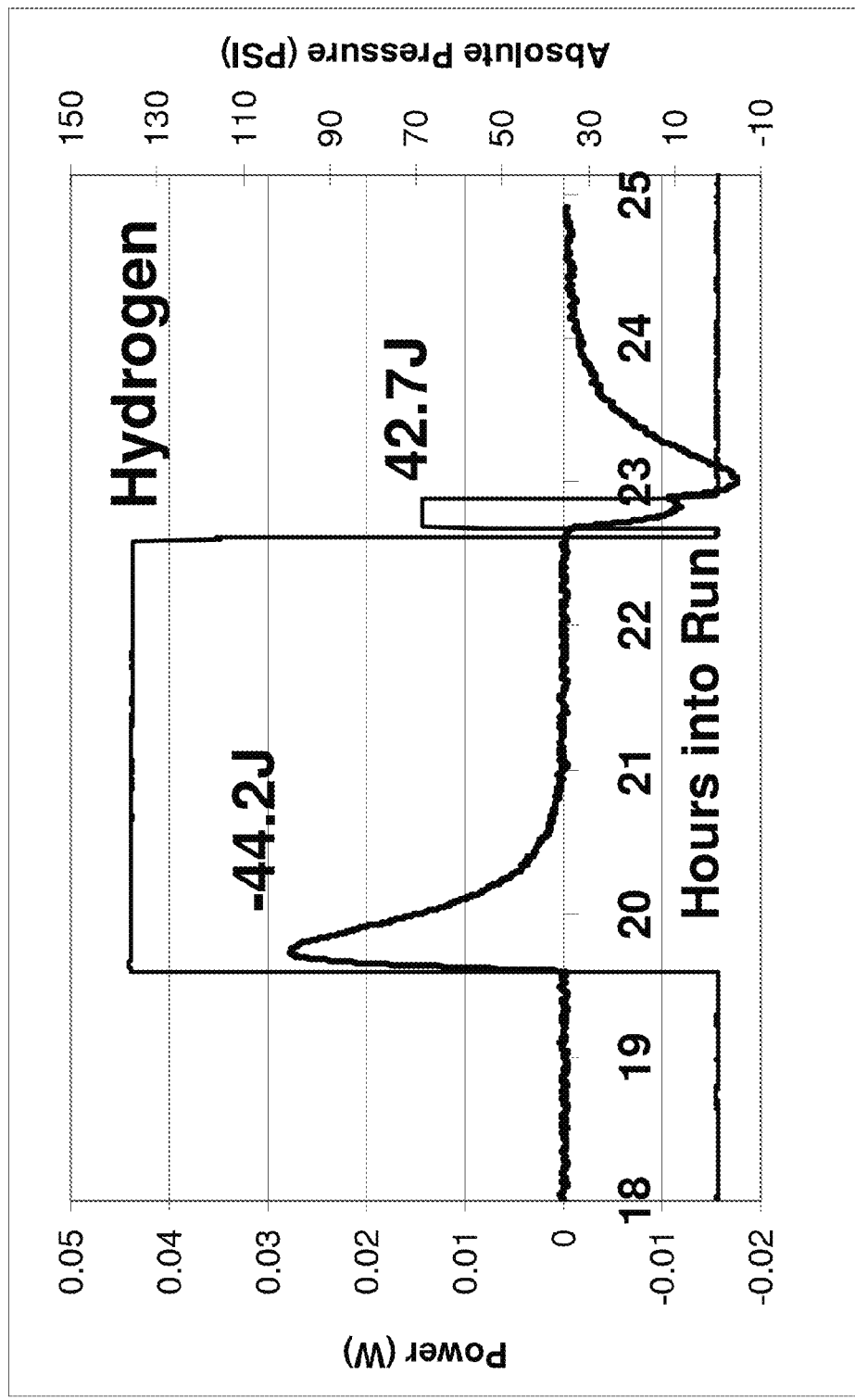
FIG. 1 shows the pressurization-depressurization cycle for hydrogen.

The present invention is directed towards producing dispersed metal particles 2 nm or less in size in a support that reduces sintering and particle growth during pressurization-depressurization cycling. The present invention is also directed towards showing that such particles display an enthalpy difference between pressurization and depressurization with a gas and this difference is in the presence of deuterium and not hydrogen.

There are three general methods to prepare dispersed metals on supports. (1) Incipient wetness impregnation, where a solution of metal precursor is absorbed on the support. The amount of solution is just enough to wet the support. A variation on this method is wet impregnation where the amount of solution is greater than needed to just wet the support and the excess is removed at low temperature. (2) Ion exchange, where ions associated with the support are replaced with the metal ion of interest, generally using aqueous solutions of the metal of interest. (3) Sol-gel, where solutions of the metal are suspended in a growing polymer, which is generally inorganic in nature. After forming the supported metal precursor, the support is generally dried and calcined to remove water and organics. The heating may be done in air or an inert gas or in the presence of a reducing agent such as hydrogen. However, calcining the supports used in the present invention was found detrimental to excess enthalpy production. Finally, the metal ions are reduced to metal nanoparticles with a reducing agent such as hydrogen or deuterium. This may be done at elevated temperatures.

Elevated temperatures and high metal loading appear to increase particle size above 2 nm and should be avoided during the preparation of the supported metal particles used in the present invention. Preferably the present invention is performed at low temperatures—less than 500° C. and even more preferably at less than 300° C. Moreover, gradual heating may produce better results than quick heating.

Repeated pressurization-depressurization cycling of a supported catalyst can cause sintering and particle growth. This problem may be reduced by encapsulating the metal particles in a matrix such as a zeolite, a sol-gel, or a protective polymer. D. G. Narehooda et al., "X-ray diffraction and H-storage in ultra-small palladium particles," *International Journal of Hydrogen Energy*, 34, 952-960 (2009), the entire contents of which are incorporated herein by reference. The use of zeolites as supports for metal particles is well-known in the art. For example, see K. P. Prasanth et al., "Hydrogen uptake in palladium and ruthenium exchanged zeolite X," *Journal of Alloys and Compounds*, 466, 439-446 (2008); Kh. M. Minachev et al., "Deuterium Exchange with the Surface of Zeolite Catalysts 5. Palladium-Containing Zeolites," Academy of Sciences of the USSR, Moscow. Translated from Izvestiya Akademii Nauk SSSR, Seriya Khimicheskaya, No. 12, pp. 2678-2682, December, 1978; J. Michalik et al., "Studies of the Interaction of $Pd^{3+}$ and $Pd^+$ with Organic Adsorbates, Water, and Molecular Oxygen in Pd—Ca—X Zeolite by Electron Spin Resonance and Electron Spin-Echo Modulation Spectroscopy," *J. Phys. Chem.*, 89, 4553-4560 (1985), the entire contents of each are incorporated herein by reference.

Many zeolites have a porous structure with defined size porous cages and are thus frequently used as catalysts supports. Zeolites are ideal for using ion-exchange methods of impregnation of the metal ion precursors as they can contain alkali-metal ions that may be easily exchanged for the metal ion of interest. If the preparation conditions for placing the ionic metal precursors in the zeolite and their reduction to metal particles are mild, the metal particles will grow inside the zeolite cage and the growth limited to the cage size. More severe metal growth conditions can cause the particles to grow outside of the zeolite cages or burst the crystal structures. See P. Gallezot et al., "X-Ray Diffraction Study of Palladium Y Zeolite Location of Palladium Acorns before and after Hydrogen Reduction," *Adv. Chem. Ser.*, 121, 66-73 (1973), the entire contents of which is incorporated herein by reference.

Measurements of excess enthalpy is conveniently done with using a gas loading apparatus. Gas loading experiments have the advantage that the system can be reversible—the heat generated upon pressurization due to the work of pressurization of the gas and the uptake of hydrogen/deuterium into the palladium matrix and spillover of that hydrogen to the support is released upon evacuation. An example of the reversibility of the work of pressurization and depressurization is shown by comparing the peaks sizes in FIGS. 1 and 2. The hydrogen produced more initial heat because it was pressurized to a higher pressure than the deuterium, yet this heat was recovered upon evacuation. This shows that reversible work is independent of the pressure of the pressurizing gas.

Excess energy (endothermic or exothermic) observed in a pressurization cycle may come from an irreversible chemical reaction. Typical reactions and processes to be considered are the initial reduction of the PdO to Pd metal and water, water (in the gas or generated) absorption by the matrix, oxidation of the hydrogen/deuterium by advantageous oxygen in the gas or absorbed on surfaces, the Joule-Thompson effect, a change in the matrix lattice with pressure, or D-H exchange with water in the matrix or surface hydroxyls. Most chemical reactions produce gaseous materials that can be monitored by sampling the gas in the cell or they consume the pressurization gas and cause a pressure drop and thereby signal their presence. For example, the oxidation of the hydrogen/deuterium by advantageous oxygen would show a pressure drop from consumption of the hydrogen/deuterium. All the reactions listed above should make themselves known or their effect (such as a change in lattice structure or reduction of PdO) should quickly be lost during repeated pressurization/depressurization cycles. Additionally, except for D-H exchange, pressurization with deuterium should produce similar amounts of heat as pressurization with hydrogen, i.e., any chemical isotope effect should be small.

Figure 2:
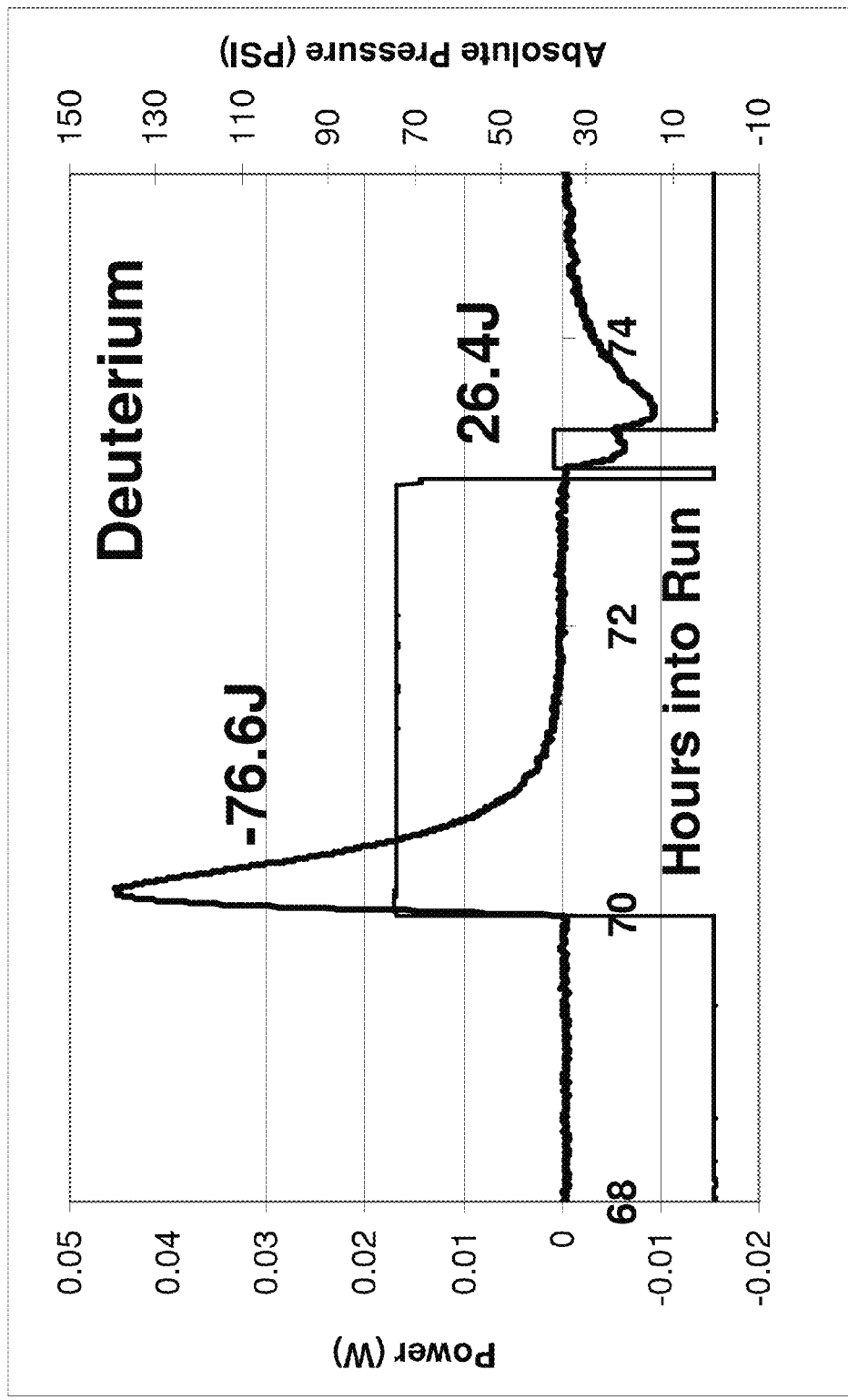
FIG. 2 shows the pressurization-depressurization cycle for deuterium.

In FIGS. 1 and 2, the pressure is shown with a thin black line and the enthalpy is shown with a thick line. The depressurization is done in steps to allow better measurement of Deuterium-Hydrogen exchange (D-H exchange) by a Residual Gas Analyzer (RGA) connected to the sampling system. D-H exchange can account for some of the excess enthalpy observed, but not all of it.

The net or excess Enthalpy during a pressurization-depressurization cycle is defined as: Excess Enthalpy=Heat During Pressurization+Heat During Depressurization. The sign of the excess enthalpy is negative if the reaction is exothermic or positive for endothermic reactions.

Surprisingly and unexpectedly, the hydrogen pressurization-depressurization cycle showed a net enthalpy of approximately zero (−1.5 J) with a ratio of Enthalpy-in/Enthalpy-out of 1.04 (44.2/42.7) (see FIG. 1). In contrast, the deuterium pressurization-depressurization cycle was quite negative showing excess enthalpy (−50.2 J) with a ratio of Enthalpy-in/Enthalpy-out of 2.9 (76.6/26.4) (see FIG. 2). Generally, the ratio is a better indication of excess enthalpy than an absolute number as it removes the amount of material being tested and calibration of the test apparatus. The ratio of Enthalpy-in/Enthalpy-out for a number of supports when pressurized/depressurized with deuterium is given in Table 2. All the ratios of the oxide supports with metal particles <2 nm in diameter are greater than one indicating excess enthalpy. In contrast, the ratio of Enthalpy-in/Enthalpy-out for a number of supports when pressurized/depressurized with hydrogen is given in Table 3. Most of these ratios are approximately one, showing no excess enthalpy.

TABLE 2

Representative Supports and Enthalpy-out/Enthalpy-in Ratio for Deuterium.
An example of the nomenclature is as follows: for H120-24h-0.1% Pd-13X,
H120 means heated at 120° C.; 24 h means 24 hours; 0.1% Pd is the
loading of Pd; and 13X is the type of support.

| | Matrix Support and metal Ion | Supplier of Support or Catalyst | Preparation Method | Enthalpy-out/Enthalpy-in | Notes |
|---|---|---|---|---|---|
| 1 | 5% Pd on BaCO$_3$ | Alfa-Aesar Cat #11721 | Commercial | 1.06 | |
| 2 | 5% Pd on Al$_2$O$_3$ pellets | Alfa-Aesar Cat #41825 | Commercial | 0.98 | |
| 3 | 0.5% Pd on Carbon | Sud Chemie | Commercial | 1.07 | |
| 4 | Zr65%—Pd35% | Santoku, Japan | Commercial | 0.99 | Arc melt-spin-cast alloy, then oxidize in air |
| 5 | Ni30%—Zr69.5%—Pd 0.5% | Prepared at NRL | Arc melt-spin-cast alloy, then oxidize in air | 1.27 | |
| 6 | Ni30%—Zr69%—Pd 1% | Prepared at NRL | Arc melt-spin-cast alloy, then oxidize in air | 0.89 | |
| 7 | Ni30%—Zr68%—Pd 2% | Prepared at NRL | Arc melt-spin-cast alloy, then oxidize in air | 1.1 | |
| 8 | Ni30%—Zr64%—Pd 4% | Prepared at NRL | Arc melt-spin-cast alloy, then oxidize in air | 0.95 | |
| 9 | H120-24h-0.5% Pd-HAZ | Prepared at NRL | Example 1 | 3.58 | |
| 10 | H120-24h-0.5% Pd—Nd-HAZ | High Alumina Zeolite - Praxair NaK-LSX | Example 6 | 3.20 | |

TABLE 2-continued

Representative Supports and Enthalpy-out/Enthalpy-in Ratio for Deuterium.
An example of the nomenclature is as follows: for H120-24h-0.1% Pd-13X,
H120 means heated at 120° C.; 24 h means 24 hours; 0.1% Pd is the
loading of Pd; and 13X is the type of support.

| | Matrix Support and metal Ion | Supplier of Support or Catalyst | Preparation Method | Enthalpy-out/Enthalpy-in | Notes |
|---|---|---|---|---|---|
| 11 | H120-24h-0.5% Pd—Eu-HAZ | High Alumina Zeolite - Praxair NaK-LSX | Example 6 | 3.14 | |
| 12 | H120-24h-0.5% Pd—Dy-HAZ | High Alumina Zeolite - Praxair NaK-LSX | Example 6 | 3.28 | |
| 13 | H120-24h-0.5% Pd—Pr-HAZ | High Alumina Zeolite - Praxair NaK-LSX | Example 6 | 3.36 | |
| 14 | H120-24h-0.5% Pd—Y-HAZ | High Alumina Zeolite - Praxair NaK-LSX | Example 6 | 4.64 | |
| 15 | H120-22h-0.5% Pd—Tm-HAZ | High Alumina Zeolite - Praxair NaK-LSX | Example 6 | 3.56 | |
| 16 | H120-22h-0.5% Pd—Er-HAZ | High Alumina Zeolite - Praxair NaK-LSX | Example 6 | 3.76 | |
| 17 | H120-22h-0.5% Pd—Ho-HAZ | High Alumina Zeolite - Praxair NaK-LSX | Example 6 | 3.59 | |
| 18 | H120-22h-0.5% Pd—Gd-HAZ | High Alumina Zeolite - Praxair NaK-LSX | Example 6 | 4.38 | |
| 19 | Unheated 0.5% Pd on HAZ | High Alumina Zeolite - Praxair NaK-LSX | Example 6 | 2.53 | Sample heated to about 300° C. under vacuum after reduction to nanoparticles |
| 20 | H120-25h-1% Pd BaTiO$_3$ + 50 uL octyl amine | Aldrich | Example 2 | 1.03 | Octyl amine added after reduction |
| 21 | H120-25h-1% Pd BaTiO$_3$ | Aldrich | Example 2 | 1.09 | |
| 22 | H120-115h-0.5% Pt 13X | Aldrich | Example 1 | 3.67 | Pt(NH$_3$)$_4$Cl$_2$ was purchased from Alfa Aesar and dissolved in water |
| 23 | H120-100h-1% Pd 13X-HFAA | Aldrich | Example 3 | 3.59 | |
| 24 | H500S-4.5h-1% Pd 13X | Aldrich | Example 1 | 1.73 | Sample heated at 12° C./hr 500° C. and held for 4.5 h |
| 25 | H500E-4.5h-1% Pd 13X | Aldrich | Example 1 | 1.60 | Sample placed in 500° C. oven and held for 4.5 h |
| 26 | H500S-4.5h-1% Pd 13X-with 1 mL of D$_2$O | Aldrich | Example 1 | 1.67 | Sample heated at 12° C./hr 500° C. and held for 4.5 h, cooled, and 1 mL of D$_2$O added before reduction |
| 27 | H120-3h-1% Pd-13X | Kurt J. Lesker Company, pellets hand powdered | Example 1 | 2.36 | H120-3h-1% Pd-13X |
| 28 | H120-4h-1% Pd—Cu-13X | Kurt J. Lesker Company, pellets hand powdered | Example 1 | 5.52 | Zeolite exchanged with Cu after adding Pd |
| 29 | H120-4.5h-1% Pd—Li-13X | Kurt J. Lesker Company, pellets hand powdered | Example 1 | 8.34 | Zeolite exchanged with Li after adding Pd |
| 30 | H120-4h-1% Pd—Pt-13X | Kurt J. Lesker Company, pellets hand powdered | Example 1 | 4.40 | Zeolite exchanged with Pt after adding Pd |
| 31 | H120-3h-1% Pd—Ni-13X | Kurt J. Lesker Company, pellets hand powdered | Example 1 | 3.9 | Zeolite exchanged with Ni after adding Pd |
| 32 | H450-8h-1% Pd—W-13X | Kurt J. Lesker Company, pellets hand powdered | Example 1 | 2 | Mixture of metals, Tungstain added as insoluble oxide |
| 33 | H120-10h-1% Pd—Al$_2$O$_3$ | Fischer Scientific | Example 2 | 1.6 | |
| 34 | H450-12h-1% Pd—Al$_2$O$_3$ | Fischer Scientific | Example 2 | 2.32 | |
| 35 | H120-10h-2% Pd—Al$_2$O$_3$ | Fischer Scientific | Example 2 | 1.64 | |
| 36 | H450-12h-2% Pd—Al$_2$O$_3$ | Fischer Scientific | Example 2 | 2.57 | |
| 37 | H120-24h-0.1% Pd-13X | Aldrich | Example 1 | 9.71 | |
| 38 | H450-24h-0.1% Pd-13X | Aldrich | Example 1 | 3.13 | |
| 39 | H120-16h-1% Pd-13X-PA | Aldrich | Example 4 | 1.72 | Palladium acetate (PA) used |

TABLE 2-continued

Representative Supports and Enthalpy-out/Enthalpy-in Ratio for Deuterium.
An example of the nomenclature is as follows: for H120-24h-0.1% Pd-13X,
H120 means heated at 120° C.; 24 h means 24 hours; 0.1% Pd is the
loading of Pd; and 13X is the type of support.

| | Matrix Support and metal Ion | Supplier of Support or Catalyst | Preparation Method | Enthalpy-out/Enthalpy-in | Notes |
|---|---|---|---|---|---|
| 40 | 0.5% Pt—Al$_2$O$_3$ | Fischer Scientific | Example 5 | 1.04 | |
| 41 | 0.5% Pd—Al$_2$O$_3$ | Fischer Scientific | Example 5 | 2.51 | |
| 42 | 0.5% Pt—SiO2 | Aldrich | Example 5 | 1.62 | Rapid decrease in excess enthalpy with pressurization-depressurization cycles |
| 43 | H120-25h-1% Pd—BaTiO$_3$ | Aldrich | Example 2 | 1.84 | |
| 44 | H120-25h-1% Pd—SrTiO$_3$ | Aldrich | Example 2 | 1.43 | |
| 45 | H120-25h-1% Pd—CaTiO$_3$ | Aldrich | Example 2 | 1.40 | |
| 46 | H120-25h-1% Pd—Na$_2$Ti$_3$O$_7$ | Aldrich | Example 2 | 1.16 | |
| 47 | H120-25h-1% Pd—Li$_2$TiO$_3$ | Aldrich | Example 2 | 1.36 | |
| 48 | H120-25h-Pd—TiO$_2$ | Aldrich | Example 2 | 1.50 | |
| 49 | H120-18h-1% Pd-CBV10A | Zeolyst International | Example 1 | 22 | |
| 50 | H120-18h-1% Pd-CP814E | Zeolyst International | Example 1 | 10 | |
| 51 | H120-18h-1% Pd-CBV5524G | Zeolyst International | Example 1 | 15.7 | |
| 52 | H450-4h-1% Pd-CBV5524G | Zeolyst International | Example 1 | 14.5 | |
| 53 | H120-18h-1% Pd-CBV10A | Zeolyst International | Example 1 | 2.4 | |
| 54 | H120-18h-1% Pd-CP814E | Zeolyst International | Example 1 | 8.9 | |
| 55 | H120-18h-1% Pd-CBV5524G | Zeolyst International | Example 1 | 9.3 | |
| 56 | H450-4h-1% Pd-CBV5524G | Zeolyst International | Example 1 | 6.6 | |
| 57 | H450-1h-0.5% Pd-Li-CP814c | Zeolyst International | Example 1 | 2.06 | Zeolite exchanged with Li after adding Pd |

TABLE 3

Representative Supports and Enthalpy-out/Enthalpy-in Ratio for Hydrogen

| Matrix Support and metal Ion | Supplier of Support or Catalyst | Preparation Method | Enthalpy-out/Enthalpy-in | Notes |
|---|---|---|---|---|
| H120-22h-0.5% Pd—Tm-HAZ | High Alumina Zeolite-Praxair NaK-LSX | Example 6 | 1.04 | |
| H120-22h-0.5% Pd—Er-HAZ | High Alumina Zeolite-Praxair NaK-LSX | Example 6 | 0.80 | |
| H120-22h-0.5% Pd—Ho-HAZ | High Alumina Zeolite-Praxair NaK-LSX | Example 6 | 0.66 | |
| H120-22h-0.5% Pd—Gd-HAZ | High Alumina Zeolite-Praxair NaK-LSX | Example 6 | 0.77 | |
| H120-22h-0.5% Pd-HAZ | High Alumina Zeolite-Praxair NaK-LSX | Example 6 | 0.78 | |
| H120-24h-0.5% Pd-HAZ | High Alumina Zeolite-Praxair NaK-LSX | Example 6 | 1.49 | |
| H120-24h-0.5% Pd—Nd-HAZ | High Alumina Zeolite-Praxair NaK-LSX | Example 6 | 1.01 | |
| H120-24h-0.5% Pd—Eu-HAZ | High Alumina Zeolite-Praxair NaK-LSX | Example 6 | 0.98 | |
| H120-24h-0.5% Pd—Dy-HAZ | High Alumina Zeolite-Praxair NaK-LSX | Example 6 | 1.13 | |

TABLE 3-continued

Representative Supports and Enthalpy-out/Enthalpy-in Ratio for Hydrogen

| Matrix Support and metal Ion | Supplier of Support or Catalyst | Preparation Method | Enthalpy-out/Enthalpy-in | Notes |
|---|---|---|---|---|
| H120-24h-0.5% Pd—Pr-HAZ | High Alumina Zeolite-Praxair NaK-LSX | Example 6 | 1.44 | |
| H120-114h-0.1% Pd-X13 | | Example 1 | 0.89 | |
| H120-114h-0.25% Pd-X13 | | Example 1 | 0.99 | |
| H120-114h-0.5% Pd-X13 | | Example 1 | 1.03 | |
| H120-72h-0.5% Pd—$Al_2O_3$ | Fischer Scientific | Example 2 | 0.85 | |
| H120-72h-1% Pd—$Al_2O_3$ | Fischer Scientific | Example 2 | 0.98 | |
| H120-72h-2% Pd—$Al_2O_3$ | Fischer Scientific | Example 2 | 1.01 | |
| H120-72h-4% Pd—$Al_2O_3$ | Fischer Scientific | Example 2 | 0.99 | |

Figure 3:
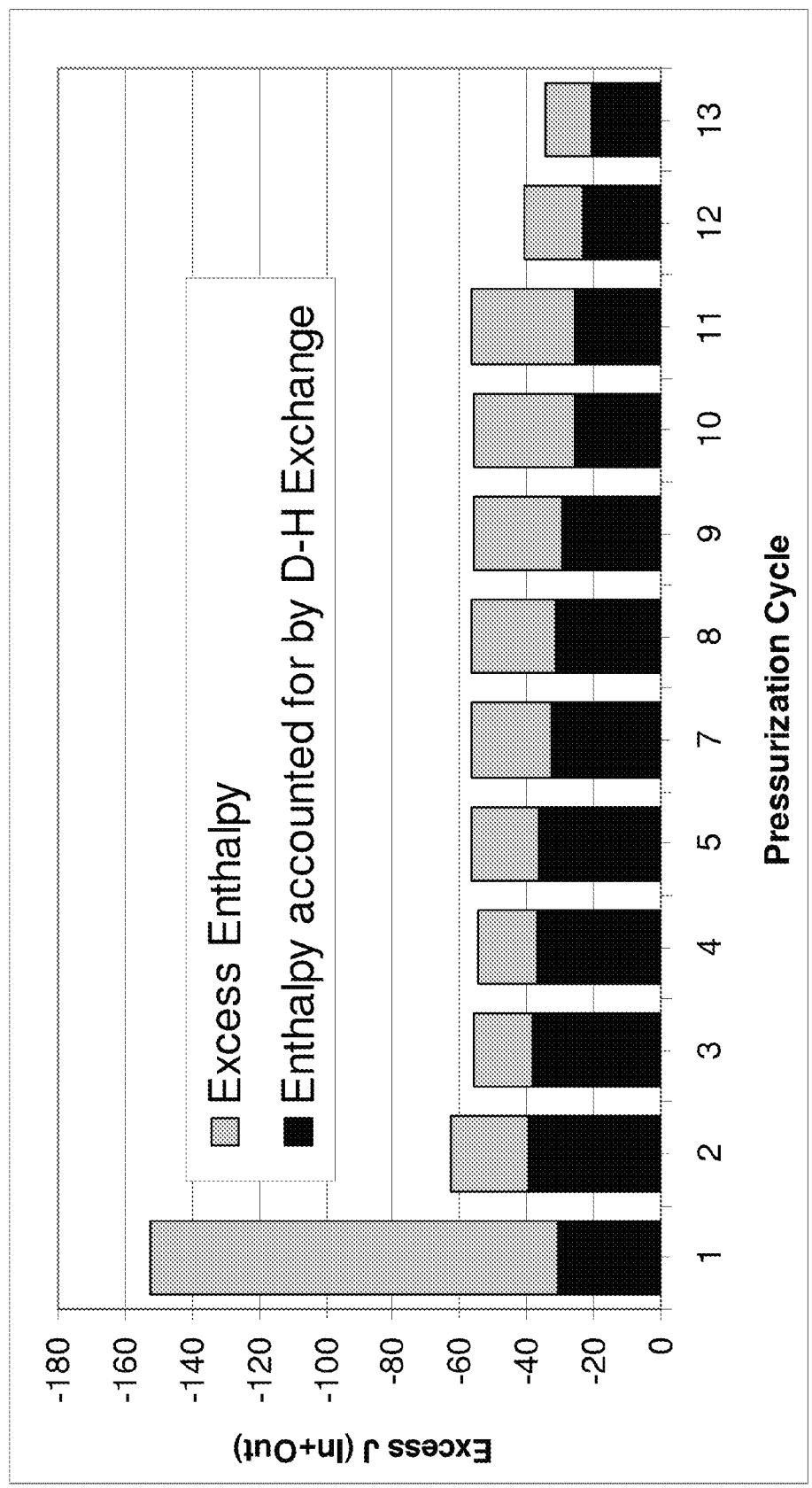
FIG. 3 is a graph showing excess enthalpy for each pressurization-depressurization cycle for 15.42 grams of 1% Pd on alumina. The alumina was dried at 120° C. for 3 hr before use. Note that the calculated enthalpy from D-H exchange (dark bars) is not a constant fraction of the total enthalpy. Excess enthalpy has the chemistry convention of having a negative sign if it is exothermic.

FIG. 3 shows that the excess enthalpy is relatively constant with pressurization-depressurization cycle number. The fall-off after pressurization-depressurization cycle 11 is likely due to growth of the particles. The amount of enthalpy that may be accounted for by D-H exchange is shown with the dark bars. The origin of the other enthalpy is unknown. The first pressurization-depressurization cycle contains other chemistry, such as reduction of the palladium ions to the palladium nanoparticle, and the enthalpy is larger.

Example 1

Ion Exchange

Palladium chloride came from several sources but for large scale preparations, it was synthesized by dissolving Suisse 99.95% Pd in aqua regia and evaporating to dryness. The palladium-amine solution was prepared fresh each time by dissolving 1 g $PdCl_2$ in 16 mL of water+4 mL of concentrated HCl and warming. To this deep red solution was slowly added 10 mL of concentrated ammonium hydroxide. A pink precipitate formed that slowly redissolved upon warming to the light yellow tetraamine. More ammonium hydroxide was added until a clear solution was produced. The percentage palladium in the zeolite was based on palladium metal where $PdCl_2$ is assumed to be 60% Pd metal. Zeolite powder (50 g) (Aldrich Molecular Sieves 13x, Cat #283592) was placed in a 500 mL flask with 200 mL of distilled water and the required amount of palladium solution. The flask was refluxed overnight. The zeolite was filtered and washed three times with warm water. The material was air dried overnight then dried at various temperatures, generally 120° C. Air drying overnight or for several days appeared to produce material with the best characteristics, especially as the palladium concentration was decreased below 0.25%. Palladium in the support may be quantitated by extraction with concentrated HCl and a colorimetric assay as the $PdI_2$ salt.

Example 2

Wet Impregnation

Alumina (50 g, Fischer Scientific Alumina Adsorption Cat #A-540) was placed in a 500 mL flask and slurried with water. The required amount of palladium solution, as prepared in Example 1, was added and the excess water removed on a RotoVapor system under aspirator pressure and at <60° C. to a semi-dry, flowing powder. This was air dried overnight and then dried at 120° C. for varying lengths of time.

Example 3

Wet Impregnation with Molecular Palladium Catalysts

Zeolite (20 g, Aldrich Molecular sieves, 13x, powder, Cat #283592) was placed in a 500 mL flask and slurried with approximately 100 mL of methylene chloride. 1 g of palladium (II) hexafluoroacetylacetonate (Aldrich Cat#401471, 20% Pd) dissolved in 11 mL of methylene chloride was added. The methylene chloride was removed on a RotoVapor system under aspirator pressure to a flowing powder containing 1% palladium metal. The powder was then dried in an air oven at 120° C. This material when pressurized remained tan in color, indicating that the particles remained very small.

Example 4

Wet Impregnation with Organic Palladium Catalysts

Zeolite (20 g, Aldrich Molecular sieves, 13x, powder, Cat #283592) was placed in a 500 mL flask and slurried with approximately 50 mL of methylene chloride. 171 mg of palladium (II) acetate (Strem Chemical, Inc. Cat#46-1780, 47% Pd) dissolved in methylene chloride was added. The methylene chloride was removed on a RotoVapor system under aspirator pressure to a flowing powder containing 0.4% palladium metal. The powder was then dried in an air oven at 120° C.

Example 5

Dispersion of Preformed Metal Particles

Metal colloids may be made though standard procedures, such as the polyol synthesis, isolated, suspended in ethyl alcohol and dispersed on dried supports though sonication in ethyl alcohol.

Example 6

Addition of Other Cations

Palladium loaded zeolite was prepared as in Example 1 but only air dried. To 10 g of palladium loaded zeolite was added 40 mL of distilled water and approximately 100 mg of rare earth nitrate salt. This was placed on a rocker at room temperature overnight. Then the sample was heated in a water bath for approximately 20 min., filtered, washed, and air dried before further processing.

Example 7

Heating of the Matrix Before Use and Testing

Figure 7:
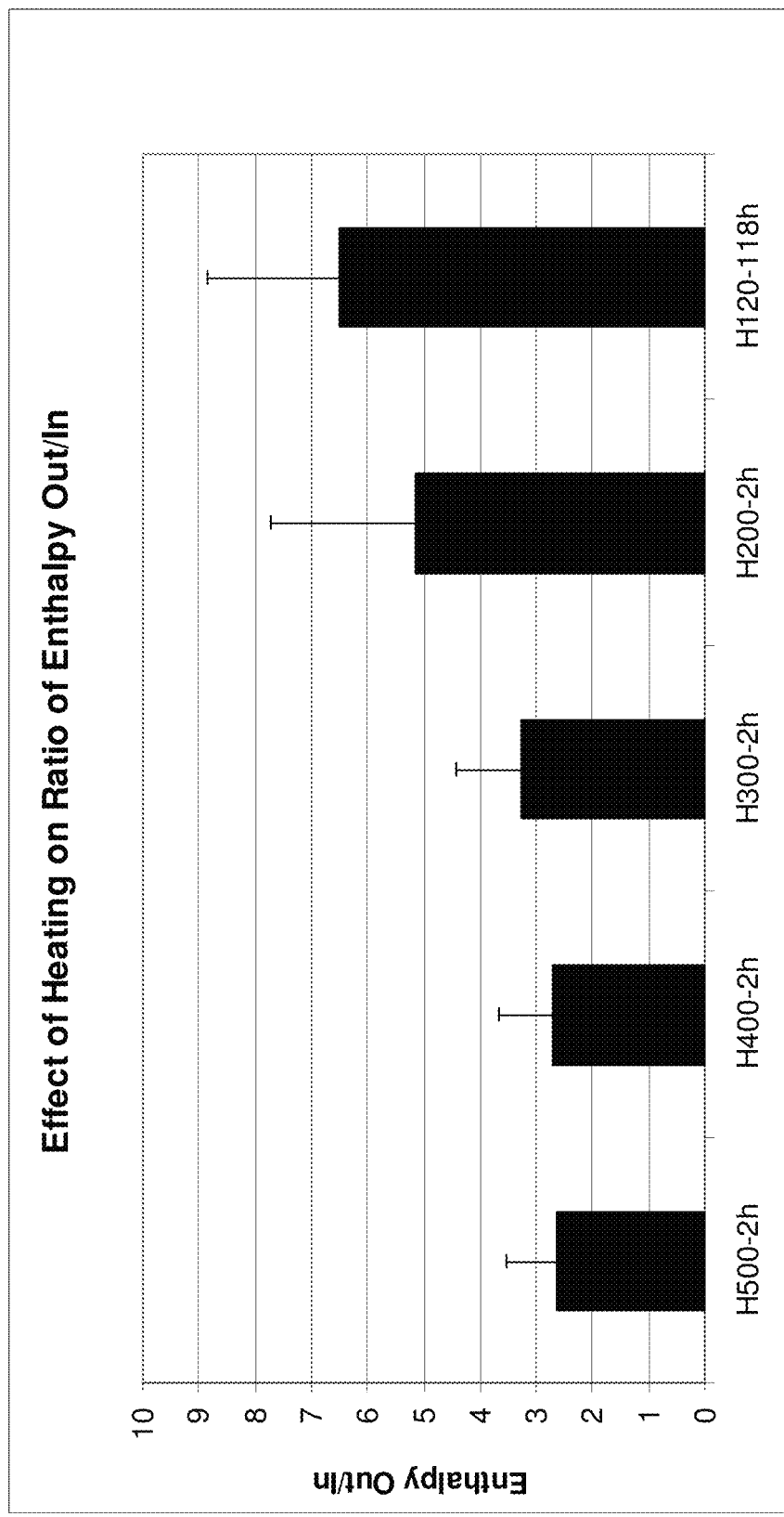
FIG. 7 is a graph showing the effects of heating on the ratio of excess enthalpy (enthalpy exothermic/enthalpy endothermic). The palladium loaded zeolite was heated to the listed temperature for the indicated time as listed in Example 7. The data was an average of pressurization-depressurization cycle 2-4. The higher heated materials had less of a decrease in excess enthalpy with pressurization-depressurization cycle number and thus the error bars are smaller.

A 100 g sample of Zeolite 13X was prepared as in Example 1 to contain 1% palladium. Approximately four 10 g samples were taken and heated to various temperatures in the following manner. All the samples were placed in an oven that was ramped to 200° C. in air. The oven was maintained at this temperature for two hours and one sample removed and cooled in a desiccator. The oven was then ramped to 300° C., held for two hours, and a second sample removed and cooled in a desiccator. The oven was then ramped to 400° C., held for two hours, and the third sample removed and cooled in a desiccator. The oven was then ramped to 500° C., held for two hours, and the fourth sample removed and cooled in a desiccator. The remaining zeolite was placed directly in a 120° C. oven for 118 hours and also cooled in a desiccator. The samples were loaded in separate cells and tested in the isothermal oven shown schematically in FIG. 5. The ratio of integrated temperature during the pressurization cycle with deuterium (related to enthalpy out with a calibration constant) to the integrated temperature during the depressurization cycle (related to enthalpy in with the same calibration constant) is plotted in FIG. 7. This clearly shows that excess heating of the zeolite matrix is detrimental to the amount of excess enthalpy produced. The ratio calculated from the data generated using the isothermal oven shown schematically in FIG. 5 has all the validity of a calibrated calorimetric system because taking the ratios of data from the same test cell removes the calibration constant. Thus, a calibration constant need not be measured for each cell when generating ratios with the system depicted schematically in FIG. 5.

Example 8

Testing

Figure 4:
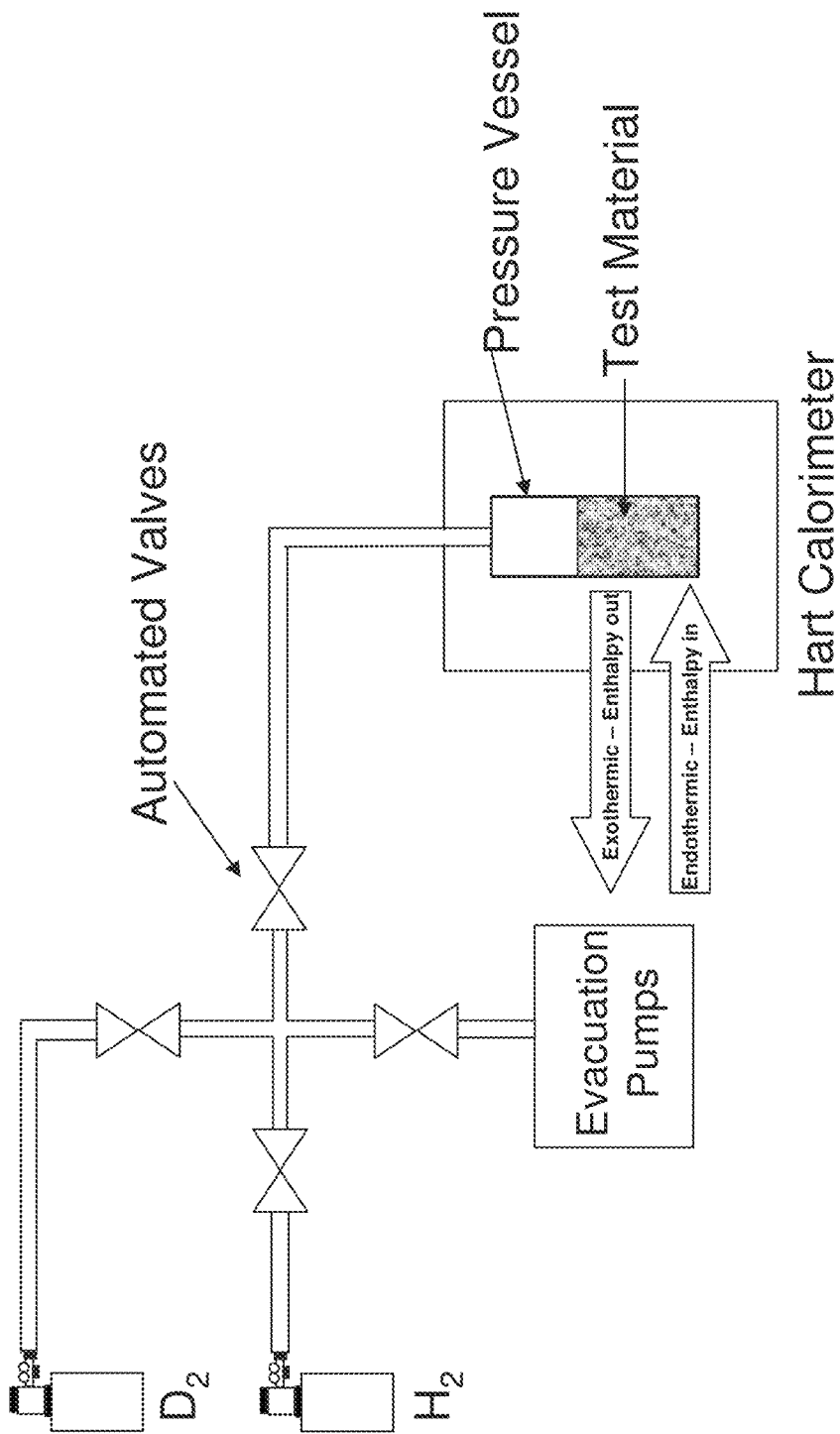
FIG. 4 is a schematic of the gas loading system using a commercial calorimeter for enthalpy measurement.

The excess enthalpy was measured on a gas loading system, as shown schematically in FIG. 4.

For operation, the test material (5-62 g of matrix) was placed in a pressure vessel, which was placed in a calorimeter (HCC-4-a Multi-cell Conduction calorimeter, Hart R & D, Inc., Mapleton, Utah). The calorimeter was calibrated electrically. After thermal equilibrium, the sample was evacuated with a roughing and then a turbo pump. Either deuterium or hydrogen was introduced. The enthalpy generated during pressurization (Enthalpy-out) was measured with the calorimeter and digitized and recorded using conventional means. The integrated area under the curve is the enthalpy of the reaction. The cell was then evacuated again with the roughing pump and turbo pump and the enthalpy taken up during depressurization (Enthalpy-in) was again measured with the calorimeter and digitized and recorded using conventional means. The formation of the metal nanoparticles was done in situ during the first pressurization-depressurization cycle and the amount of excess enthalpy was relatively large due to this chemistry occurring. A typical pressurization-depressurization cycle for hydrogen is shown in FIG. 1 and for deuterium is shown in FIG. 2.

Figure 5:
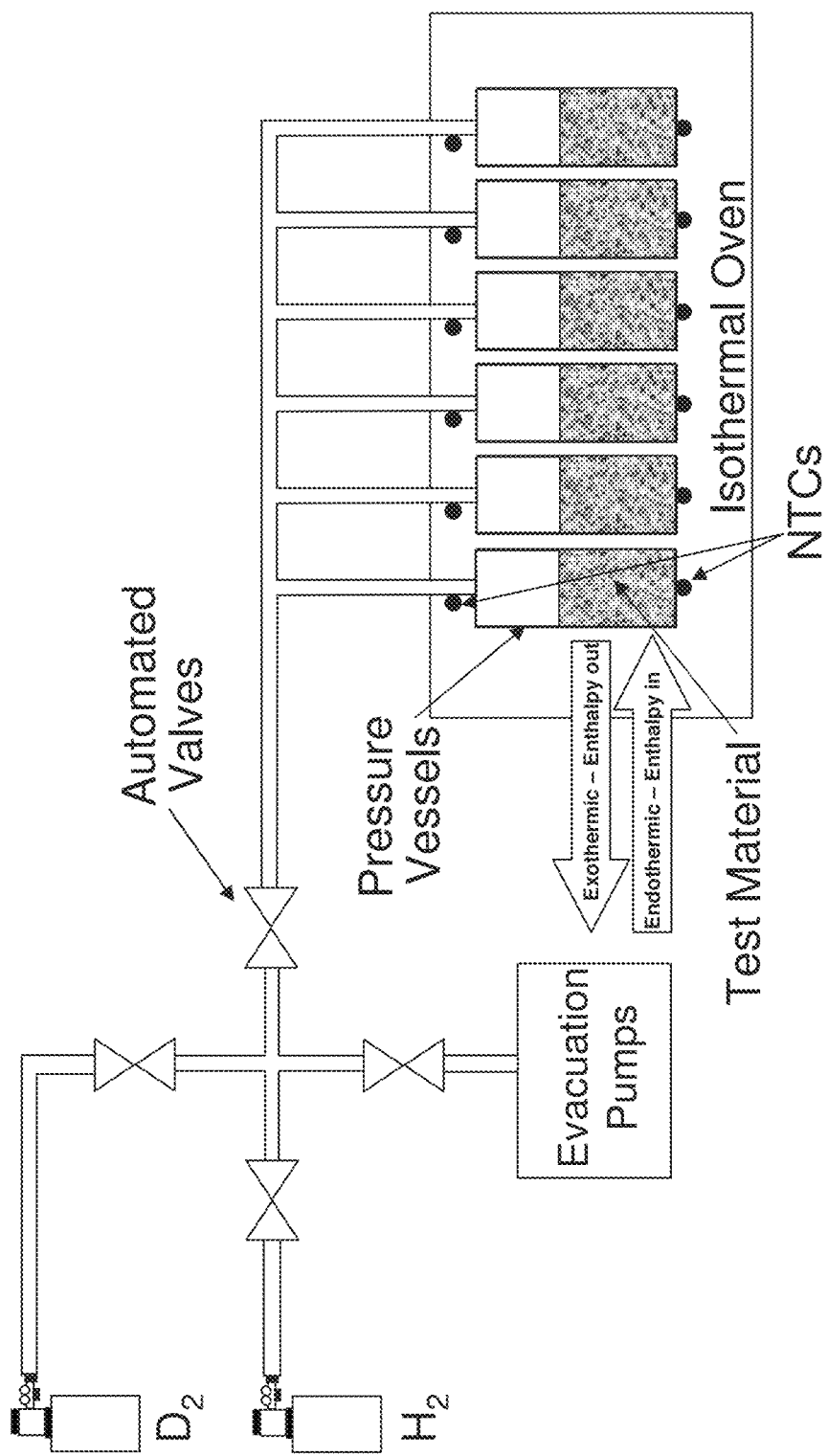
FIG. 5 is a schematic of a gas loading system having six test chambers and using thermistors for temperature measurements.

Another system for measuring excess enthalpy is shown schematically in FIG. 5. This system has six identical cells that may be pressurized or evacuated simultaneously.

For operation, the test material (5-15 g of matrix) was placed in a pressure vessel which was thermally equilibrated inside the isothermal oven. After thermal equilibrium, the sample was evacuated with a roughing pump. Either deuterium or hydrogen was introduced. The temperature change during pressurization (Temperature-out) was measured by the temperature increase on the bottom Negative Temperature Coefficient (NTC) thermistor and digitized and recorded using conventional means. The top NTC served as a control to measure variations in the oven temperature. The cell was then evacuated again with the roughing pump and the temperature change during depressurization (Temperature-in) was again digitized and recorded using conventional means. The integrated area under the curve is related to the enthalpy of the reaction by multiplication by a calibration constant. However, precise calibration is difficult between all the cells so that only the relative enthalpy is generally measured and is not needed to report the ratios given in Table 2 or Table 3. The formation of the metal nanoparticles is done in situ during the first pressurization-depressurization cycle and the amount of excess temperature is relatively large due to this chemistry occurring.

For observing excess enthalpy, the particle size should be small—2 nm or less. The matrix supporting the particles is less critical. Commercial catalysts (lines 1-3 in Table 2) have too high a loading and/or were likely made though a calcination process and thus have larger particles. Deuterium NMR is diagnostic for particle size. The commercial $Pd/BaCO_3$ and $Pd/Al_2O_3$ show deuterium absorbances that corresponding to deuterium in bulk palladium whereas the particles made in Examples 1, 2, and 3 show only broad absorbances at NMR positions, different than those known for deuterium in bulk palladium. The commercial, supported palladium catalysts show no excess enthalpy.

Observation of nanoparticles 2 nm or less in size in a zeolite matrix is difficult by conventional Transmission Electron Microscopy (TEM) (P. C. Aben). The size of the majority of the particles made by Examples 1 and 2 were not observable by conventional TEM indicating that they were less than 5 nm in diameter. Only a few of the larger particles, which grew outside of the zeolite matrix were visible, and they were about 1-2 nm diameter. Energy dispersive X-ray (EDX) analysis showed that palladium was throughout the matrix rather than localized as indicated by the TEM. Likewise, powder X-ray diffraction was not able to see the palladium nanoparticles, also indicating that they were less than 5 nm in diameter. Aberration-corrected TEM did show a multitude of small particles 0.5-1 nm in diameter throughout the matrix, but this instrumentation was unavailable for characterization of the majority of the samples prepared.

The materials of the present application are quite distinct from those in the literature. Arata's particles (ca. 5 nm) are much larger than the particles described in the present application (Arata et al., *Formation of Condensed Metallic Deuterium Lattice and Nuclear Fusion*. Proc. Jpn. Acad., Ser. B, 78 (Ser. B): p. 57 (2002)). Furthermore, they sinter during use. Using materials prepared to Arata's formula and similar matrices has failed to produce excess enthalpy when tested using our pressurization procedures (Table 2, Lines 4-8).

Figure 6:
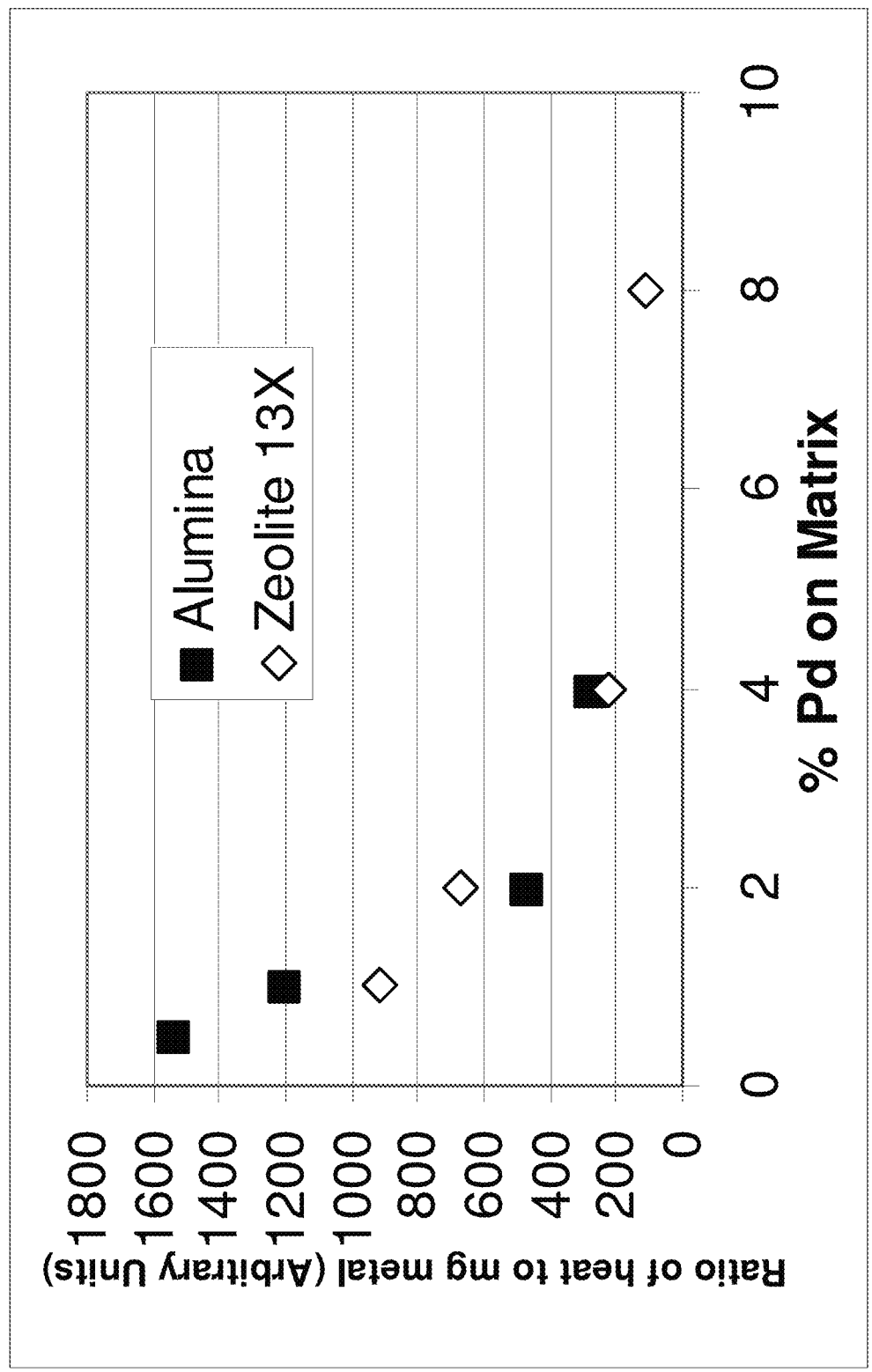
FIG. 6 is a graph showing the effect of palladium loading of the matrix on excess enthalpy produced. The samples were tested in the isothermal system that only produces relative enthalpies. The second pressurization cycle with deuterium was used in these calculations. The alumina was prepared using Example 2 and the zeolite was prepared using Example 1.

Lower metal loadings also favor smaller particle sizes. FIG. 6 shows how the excess enthalpy varies with loading; the lower the loading the larger the excess enthalpy relative to the amount of metal. However, the absolute amount of enthalpy also decreases with loading. The absolute amount of enthalpy reaches a maximum at around 1% palladium, depending on the support and the exact preparation conditions.

The above descriptions are those of the preferred embodiments of the invention. Various modifications and variations are possible in light of the above teachings without departing from the spirit and broader aspects of the invention. It is therefore to be understood that the claimed invention may be

What is claimed as new and desired to be protected by Letters Patent of the United States is:

1. A method for measuring excess enthalpy, comprising:
    placing a test material in a pressure vessel;
    heating the pressure vessel to a given temperature;
    evacuating the pressure vessel;
    introducing deuterium, hydrogen, or both into the pressure vessel;
    measuring the enthalpy generated during pressurization;
    again evacuating the pressure vessel; and
    measuring the enthalpy used during depressurization.

2. The method of claim 1, wherein the test material comprises dispersed metal particles 2 nm or less in size in an oxide support that reduces sintering and particle growth.

3. The method of claim 2, wherein the metal particles comprise, palladium, platinum, or any combination thereof.

4. The method of claim 2, wherein the oxide support is a zeolite or alumina.

5. The method of claim 1, wherein the temperature is less than 300° C.

6. The method of claim 1, wherein the temperature is less than 100° C.

7. The method of claim 1, wherein when the pressure vessel is again evacuated, all of the deuterium, hydrogen, or both that was introduced into the system is removed.

8. The method of claim 1, wherein the test material is pressurized to 100 psi or below.

9. The method of claim 1, wherein the test material is pressurized to 50 psi or below.

* * * * *